US011980339B2

United States Patent
Nagata et al.

(10) Patent No.: US 11,980,339 B2
(45) Date of Patent: May 14, 2024

(54) ENDOSCOPE AND INSERTION PORTION THEREOF

(71) Applicant: OLYMPUS CORPORATION, Hachioji (JP)

(72) Inventors: Yuki Nagata, Tokyo (JP); Hiroyuki Nagamizu, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 500 days.

(21) Appl. No.: 17/157,781

(22) Filed: Jan. 25, 2021

(65) Prior Publication Data

US 2021/0137360 A1 May 13, 2021

Related U.S. Application Data

(63) Continuation of application No. PCT/JP2019/006699, filed on Feb. 22, 2019.

(30) Foreign Application Priority Data

Aug. 21, 2018 (JP) ................................. 2018-154662

(51) Int. Cl.
*A61B 1/00* (2006.01)
*A61B 1/05* (2006.01)
(Continued)

(52) U.S. Cl.
CPC ............ *A61B 1/00096* (2013.01); *A61B 1/05* (2013.01); *A61B 1/07* (2013.01); *G02B 23/2423* (2013.01)

(58) Field of Classification Search
CPC .............. A61B 1/00096; A61B 1/0008; A61B 1/00174; A61B 1/05; A61B 1/07; G02B 23/2423; G02B 23/2469
See application file for complete search history.

(56) References Cited

U.S. PATENT DOCUMENTS

2003/0233024 A1\* 12/2003 Ando ................. A61B 1/00096
600/111
2005/0089286 A1\* 4/2005 Hatori ................. A61B 1/0011
385/117
(Continued)

FOREIGN PATENT DOCUMENTS

JP 2002085326 A \* 3/2002
JP 2002085326 A 3/2002
(Continued)

OTHER PUBLICATIONS

Japanese Office Action dated Aug. 19, 2021 (and English translation thereof) issued in Japanese Application No. 2020-538019.
(Continued)

*Primary Examiner* — John P Leubecker
(74) *Attorney, Agent, or Firm* — Holtz, Holtz & Volek PC

(57) ABSTRACT

An endoscope includes: an objective optical system including a lens, allowing light from an imaging subject to be incident on a distal end surface, and focusing the light onto an image-capturing surface of an image-capturing element; an elongated light guide provided adjacent to a side of the system and guiding illumination light to be emitted from a distal end; and an optically transparent distal end cover disposed at a position where the distal end of the guide is covered, wherein the distal end surface is located farther forward than the distal end of the guide, a notched portion is provided at a distal-end outer edge of a side surface of the system, the side surface being adjacent to the guide, so that the system is narrower toward a front side from the distal end of the guide, and the cover is provided so as to bulge toward the notched portion.

20 Claims, 11 Drawing Sheets

(51) Int. Cl.
    *A61B 1/07*     (2006.01)
    *G02B 23/24*     (2006.01)

(56) References Cited

U.S. PATENT DOCUMENTS

| | | | |
|---|---|---|---|
| 2007/0249907 A1* | 10/2007 | Boulais | A61B 5/064 600/179 |
| 2008/0242935 A1* | 10/2008 | Inoue | A61B 1/07 600/176 |
| 2010/0027135 A1* | 2/2010 | Sodeyama | G02B 7/021 359/740 |
| 2011/0157574 A1* | 6/2011 | Kato | A61B 1/00096 355/71 |
| 2015/0241607 A1* | 8/2015 | Mori | G02B 23/243 359/819 |
| 2017/0209030 A1* | 7/2017 | Nakao | A61B 1/0055 |
| 2017/0307872 A1* | 10/2017 | Hatase | H04N 23/51 |
| 2018/0020134 A1* | 1/2018 | Haraguchi | A61B 1/051 |
| 2020/0201024 A1 | 6/2020 | Hatase et al. | |

FOREIGN PATENT DOCUMENTS

| | | | |
|---|---|---|---|
| JP | 2006325744 A | | 12/2006 |
| JP | 2008237790 A | | 10/2008 |
| JP | 2009207529 A | * | 9/2009 |
| JP | 2009207529 A | | 9/2009 |
| JP | 2009207578 A | | 9/2009 |
| JP | 2014155526 A | * | 8/2014 |
| JP | 2014155526 A | | 8/2014 |
| JP | 2016209411 A | | 12/2016 |
| JP | 2017195960 A | | 11/2017 |

OTHER PUBLICATIONS

International Search Report (ISR) (and English translation thereof) dated May 21, 2019 issued in International Application No. PCT/JP2019/006699.

* cited by examiner

ENDOSCOPE AND INSERTION PORTION THEREOF

CROSS-REFERENCE TO RELATED APPLICATIONS

This is a continuation of International Application PCT/JP2019/006699 which is hereby incorporated by reference herein in its entirety.

This application is based on Japanese Patent Application No. 2018-154662, the contents of which are incorporated herein by reference.

TECHNICAL FIELD

The present invention relates to an endoscope and an insertion portion thereof.

BACKGROUND ART

There is a known endoscope device using, as an objective optical system, a laminated optical system in which an optical element is directly molded and bonded onto an image-capturing element by means of a semiconductor process (for example, see Patent Literature 1). As compared with conventional optical systems, a laminated optical system does not require a frame for holding the laminated optical system, and in addition, the number of processes involving advanced skills can be reduced by using an electric assembly device; thus, a reduction in size and cost can be expected. In the endoscope device described in Patent Literature 1, the distal end of an endoscope is made compact by means of the laminated optical system.

CITATION LIST

Patent Literature

{PTL 1} Japanese Unexamined Patent Application, Publication No. 2017-195960

SUMMARY OF INVENTION

An aspect of the present invention is an endoscope including: an objective optical system including a lens, the objective optical system allowing light from an imaging subject to be incident on a distal end surface and focusing the light onto an image-capturing surface of an image-capturing element; an elongated light guide that is provided adjacent to a side of the objective optical system and that guides illumination light from a light source to be emitted from a distal end; and an optically transparent distal end cover that is disposed at a position where the distal end of the light guide is covered, wherein the distal end surface of the objective optical system is located farther forward than the distal end of the light guide, a notched portion is provided at a distal-end outer edge of a side surface of the objective optical system, the side surface being adjacent to the light guide, so that the objective optical system is narrower toward a front side from the distal end of the light guide, and the distal end cover is provided so as to bulge toward the notched portion.

Another aspect of the present invention is an insertion portion of an endoscope including: an objective optical system including a lens, the objective optical system allowing light from an imaging subject to be incident on a distal end surface and focusing the light onto an image-capturing surface of an image-capturing element; an elongated light guide that is provided adjacent to a side of the objective optical system and that guides illumination light from a light source to be emitted from a distal end; and an optically transparent distal end cover that is disposed at a position where the distal end of the light guide is covered, wherein the distal end surface of the objective optical system is located farther forward than the distal end of the light guide, a notched portion is provided at a distal-end outer edge of a side surface of the objective optical system, the side surface being adjacent to the light guide, so that the objective optical system is narrower toward a front side from the distal end of the light guide, and the distal end cover is provided so as to bulge toward the notched portion.

DESCRIPTION OF EMBODIMENT

An endoscope device according to an embodiment of the present invention will be described below with reference to the drawings.

Figure 1:
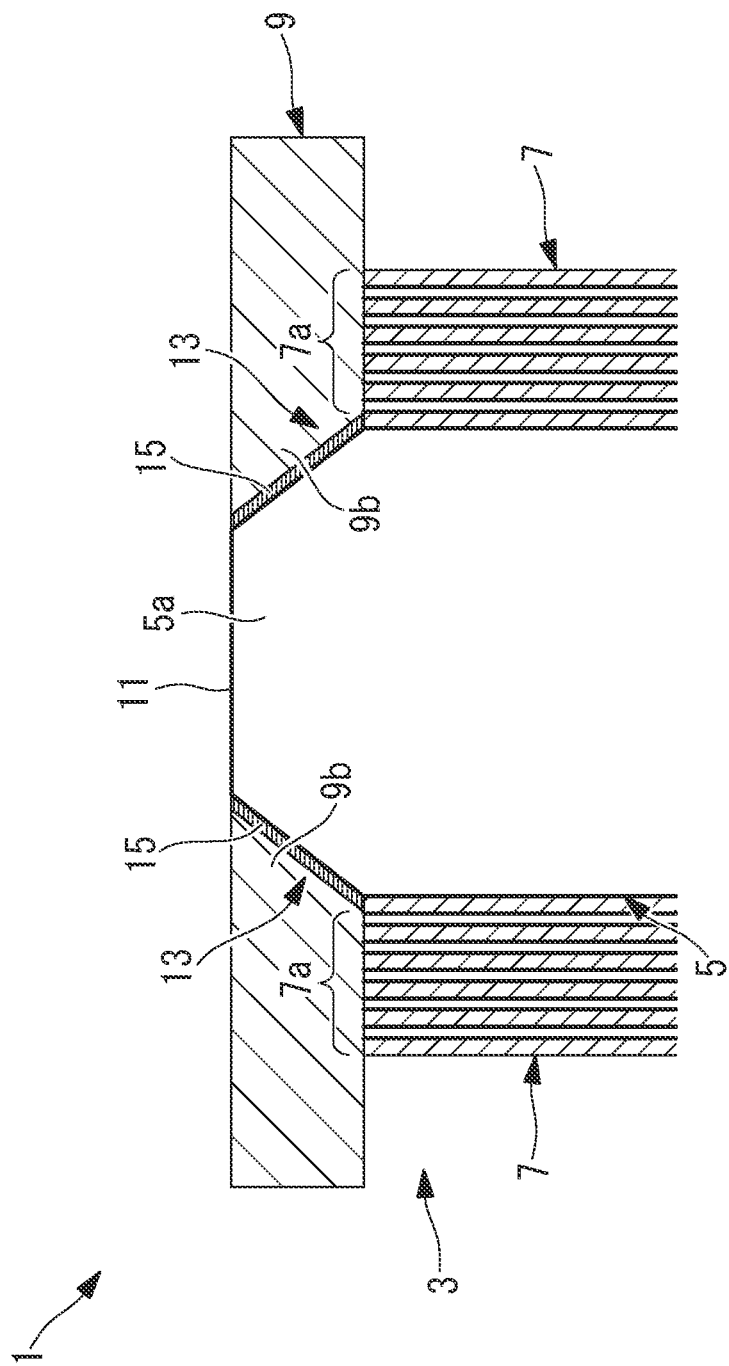
FIG. 1 is a longitudinal sectional view of a distal end portion of an endoscope device according to an embodiment of the present invention.
Figure 2:
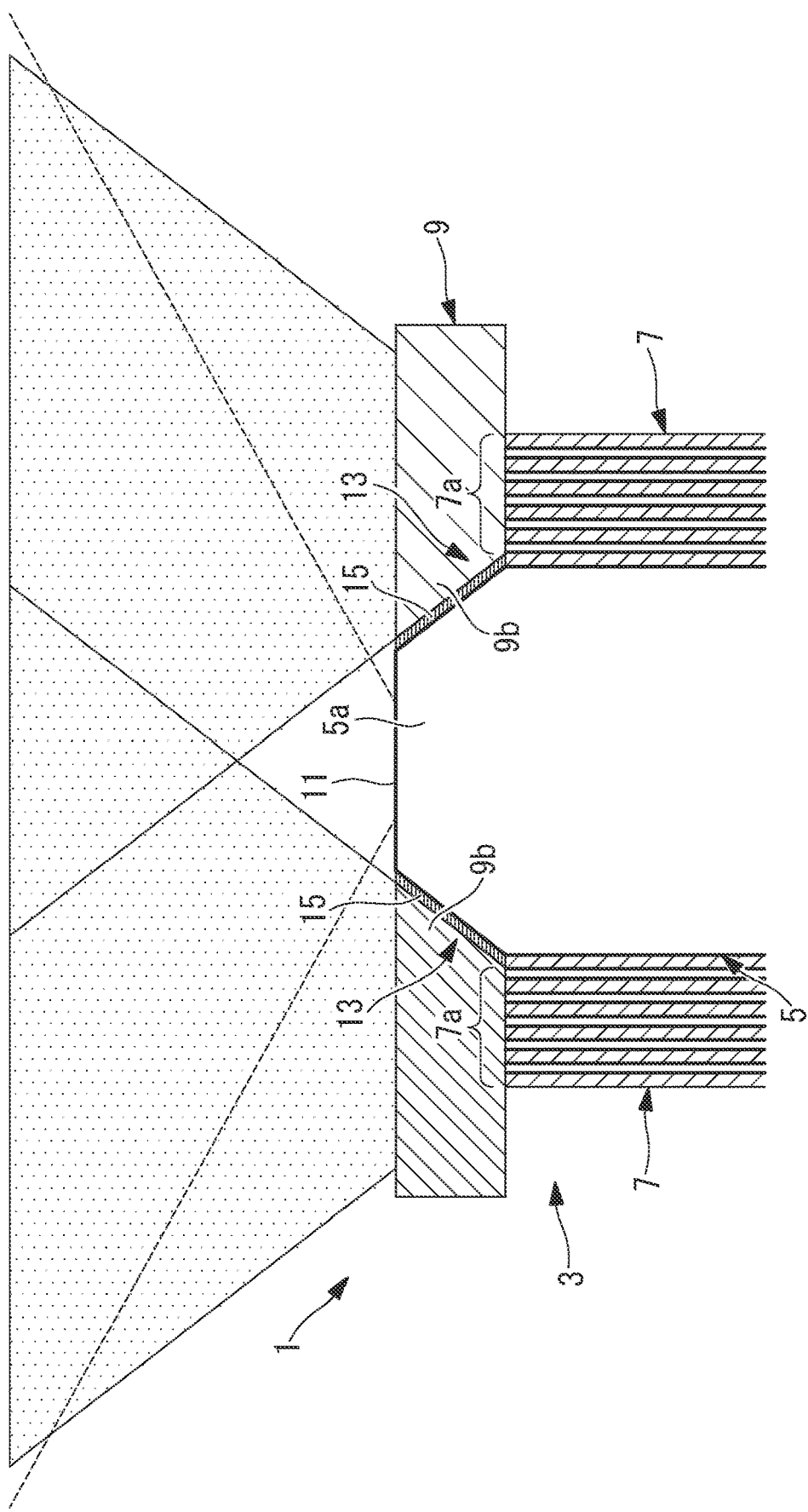
FIG. 2 is a longitudinal sectional view of the distal end portion showing a state in which illumination light is radiated toward an imaging subject from the distal end portion of the endoscope device in FIG. 1.

As shown in FIGS. 1 and 2, an endoscope device 1 according to this embodiment includes a distal end portion 3 that is provided at a distal end of an elongated insertion portion (not shown) to be inserted into a body cavity, and that has an image-capturing element (not shown) disposed in the interior thereof.

The distal end portion 3 is provided with: an objective optical system 5 that focuses light from an imaging subject (not shown) onto an image-capturing surface of the image-capturing element; two sets of elongated light guides 7 that are arranged adjacent to sides of the objective optical system 5 and that guide illumination light emitted from a light source (not shown) to be emitted from distal ends 7a; and an optically transparent distal end cover 9 that protects the distal ends 7a of the respective light guides 7.

The image-capturing element is, for example, a CCD (Charge Coupled Device), a CMOS (Complementary Metal-Oxide Semiconductor), or the like having a substantially square external shape as viewed from an optical axis direction. The image-capturing surface of the image-capturing element is covered with an element cover glass (not shown).

The objective optical system 5 is composed of, for example, a lens, an aperture stop, and an objective cover glass (all not shown) that are arranged on the image-capturing element in a laminated state, and is formed in a substantially prismatic shape. The objective optical system 5 is formed by directly molding and bonding, onto the image-capturing element, the lens, the aperture stop, and the objective cover glass in this order by using a semiconductor process.

The lens is, for example, a single lens and is formed in a prismatic shape having a substantially square cross section orthogonal to the optical axis. In addition, the lens is provided such that the optical axis is aligned with the center of the image-capturing surface of the image-capturing element, and a surface thereof on the imaging subject side is covered with the objective cover glass, with the aperture stop interposed therebetween. The element cover glass is disposed between the lens and the image-capturing element. The lens focuses the light from the imaging subject, which has passed through the objective cover glass and the aperture stop, onto the image-capturing surface of the image-capturing element via the element cover glass.

The objective optical system 5 having the abovementioned configuration is provided in a state in which a portion of the objective cover glass protrudes toward the front side of the distal ends 7a of the light guides 7. Hereinafter, the portion of the objective cover glass, which protrudes toward the front side of the distal ends 7a of the light guides 7, is referred to as a distal end portion 5a of the objective optical system 5.

The distal end portion 5a is formed in, for example, a shape having a trapezoidal longitudinal section. The distal end portion 5a is provided with: a distal end surface 11 that allows the light from the imaging subject to be incident thereon; and notched portions 13 that form the objective optical system 5 so as to be narrower toward the front side from the distal ends 7a of the light guides 7.

Figure 3:
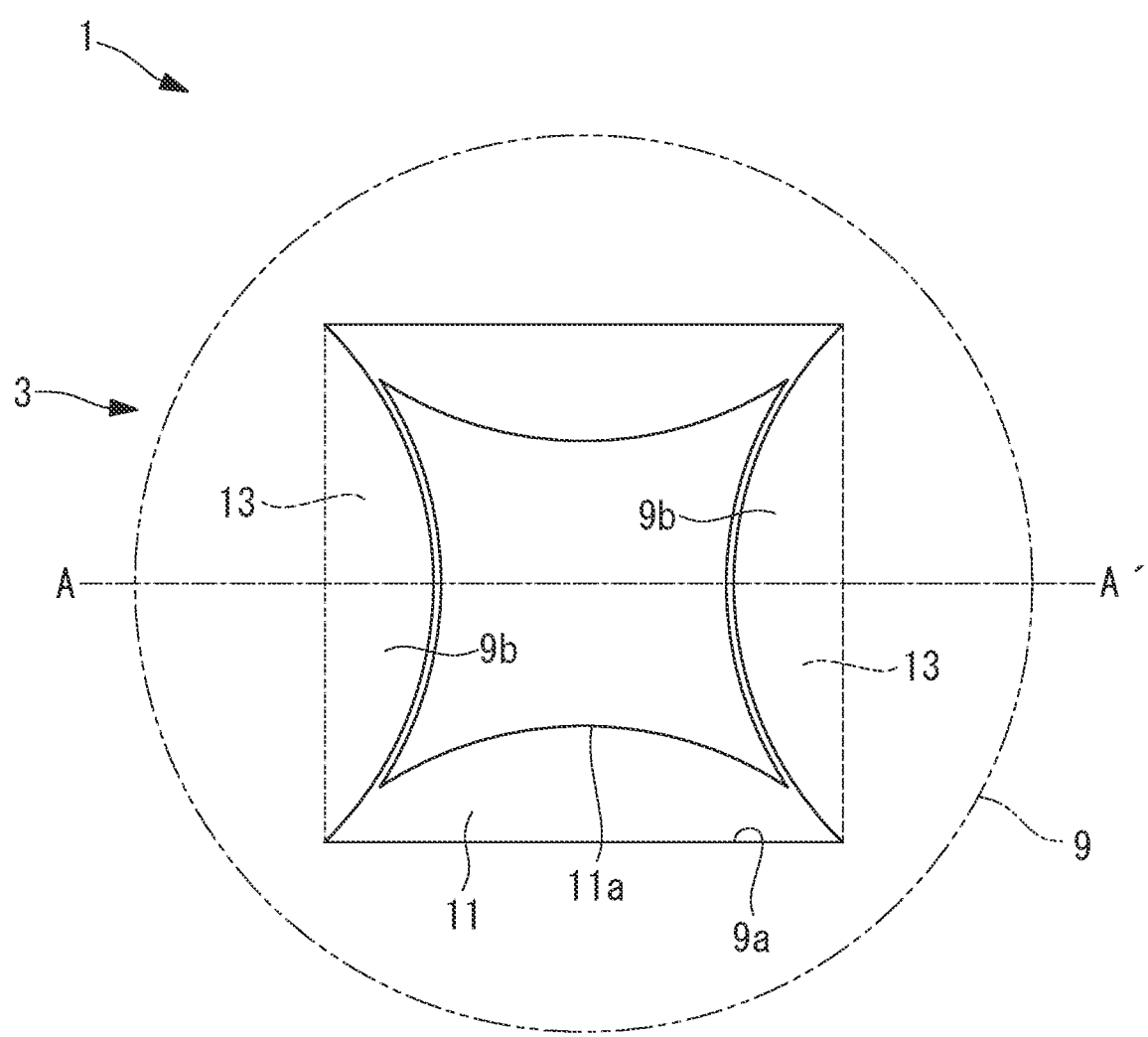
FIG. 3 is a plan view of the distal end portion of the endoscope device in FIG. 1 as viewed from the imaging subject side along an optical axis of an objective optical system.
Figure 4:
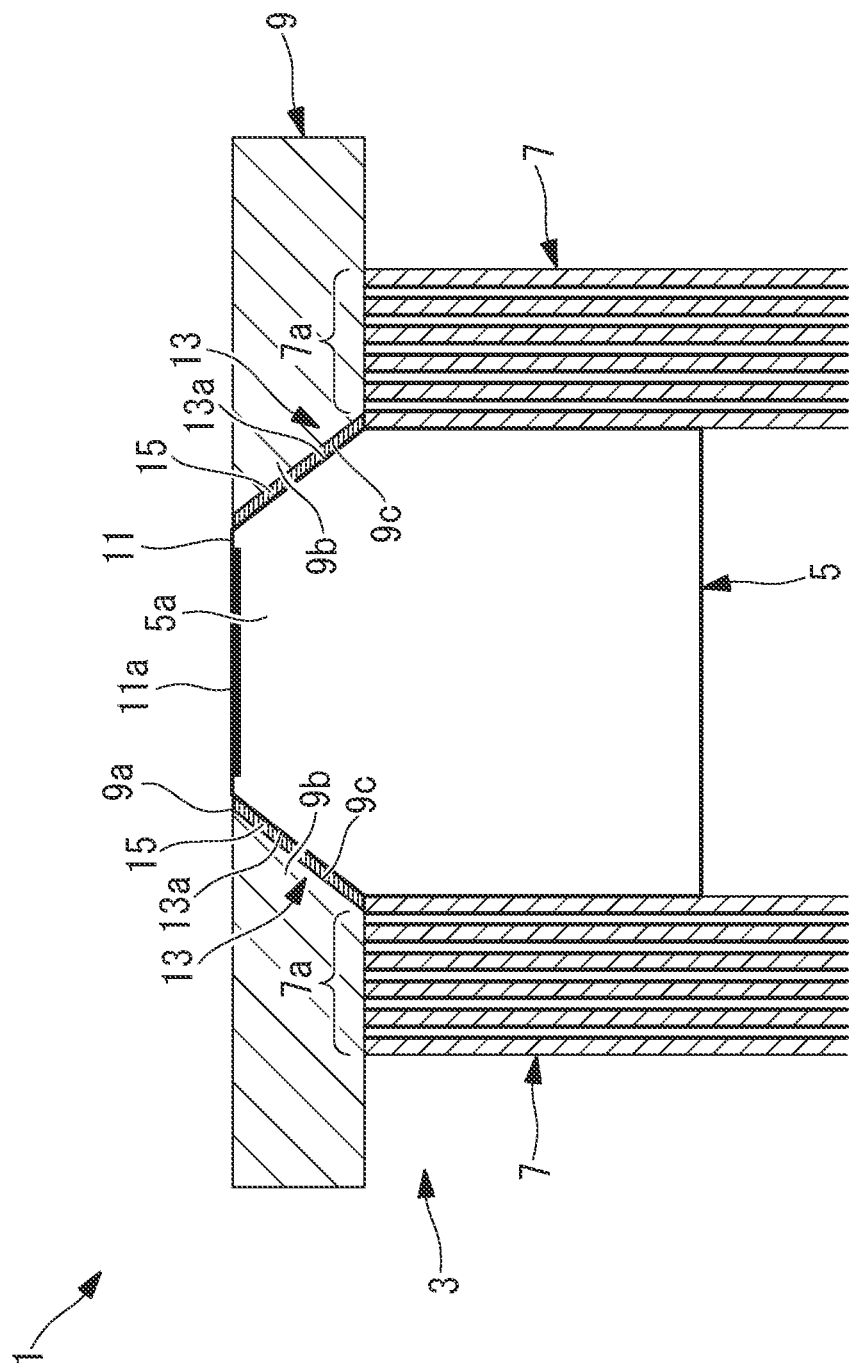
FIG. 4 is a cross-sectional view taken along A-A' in FIG. 3.

The distal end surface 11 is composed of one surface of the objective cover glass and is located farther forward than the distal ends 7a of the light guides 7 in a state in which the distal end surface 11 is orthogonal to the optical axis of the objective optical system 5. For example, as shown in FIGS. 3 and 4, an effective incident range 11a through which the light from the imaging subject, which is to be focused onto the image-capturing surface of the image-capturing element, passes is defined in the distal end surface 11. The effective incident range 11a has a substantially square external shape, and each side is formed by a smooth curve that is recessed inward. The light that has entered the objective optical system 5 from outside the effective incident range 11a is not focused onto the image-capturing surface of the image-capturing element.

The notched portions 13 are respectively provided at distal-end outer edges of both side surfaces of the objective optical system 5, the side surfaces being adjacent to the light guides 7, and are formed outside the effective incident range 11a in the distal end surface 11 of the objective optical system 5. For example, as shown in FIG. 4, the notched portions 13 have notched surfaces 13a that are inclined so that the distal end portion 5a is narrower toward the front side from the distal ends 7a of the light guides 7. The notched surfaces 13a have a smoothly curved shape that is recessed inward in a width direction of the distal end portion 5a.

The light guides 7 are arranged in a state in which the light guides 7 are adjacent to the mutually opposing side surfaces of the objective optical system 5. In the light guides 7, the distal ends 7a extend to positions nearby the distal end portion 5a of the objective optical system 5, and the other ends extend toward a proximal end of the insertion portion. Each of the light guides 7 is composed of a plurality of optical fibers that are arranged side by side along the side surface of the objective optical system 5.

For example, as shown in FIGS. 3 and 4, the distal end cover 9 has an annular external shape and has, at the center thereof, a through-hole 9a that penetrates therethrough in a thickness direction. The distal end cover 9 is entirely formed of a transparent resin. The distal end cover 9 has such external dimensions that the distal end cover 9 expands more radially outward than the light guides 7. All corners of the distal end cover 9 may be rounded, in other words, rounding may be applied to all corners. With this configuration, the diffusion effect of the illumination light is improved, thus making it possible to expand the irradiation range.

The distal end cover 9 is disposed at a position where the distal ends 7a of the light guides 7 are covered, and the distal end portion 5a of the objective optical system 5 is inserted into the through-hole 9a. The imaging-subject-side surface of the distal end cover 9 and the distal end surface 11 of the objective optical system 5 are arranged so as to be substantially flush with each other. By covering the distal ends 7a of the light guides 7 with the distal end cover 9, it is possible to protect the light guides 7, thereby improving the durability to reprocessing.

The distal end cover 9 has bulging portions 9b that bulge toward the notched portions 13 of the objective optical system 5. The bulging portions 9b are composed of inner edge portions forming the through-hole 9a and have a shape complementary to the notched portions 13 of the objective optical system 5. Specifically, the bulging portions 9b have inner surfaces 9c that are inclined, from the ends at one side toward the ends at the other side in the thickness direction, in a tapered manner in which the through-hole 9a gradually becomes smaller, and have such a shape that the bulging portions 9b cover substantially the entire areas of the notched surfaces 13a in conformity with the shape of the notched portions 13.

Light blocking portions 15 for blocking the illumination light are arranged at the boundaries between the inner surfaces 9c of the bulging portions 9b of the distal end cover 9 and the notched surfaces 13a of the notched portions 13 of the objective optical system 5. With the light blocking portions 15, the illumination light emitted from the distal ends 7a of the light guides 7 can be prevented from entering the objective optical system 5 from the notched portions 13 after passing through the bulging portions 9b of the distal end cover 9.

The operation of the endoscope device 1 having the abovementioned configuration will now be described.

In order to observe an imaging subject with the endoscope device 1 according to this embodiment, the distal end portion 3 is placed so as to face the imaging subject in a state in which the insertion portion is inserted into the body cavity, and illumination light is generated from the light source.

The illumination light emitted from the light source is guided by the light guides 7 and is subsequently emitted from the distal ends 7a of the light guides 7. The illumination light is radiated onto the imaging subject after passing through the distal end cover 9. The light from the imaging subject irradiated with the illumination light enters the effective incident range 11a of the objective optical system 5 and is subsequently focused onto the image-capturing surface of the image-capturing element by the lens of the objective optical system 5. By doing so, it is possible to acquire image information of the imaging subject in the image-capturing element.

Figure 5:
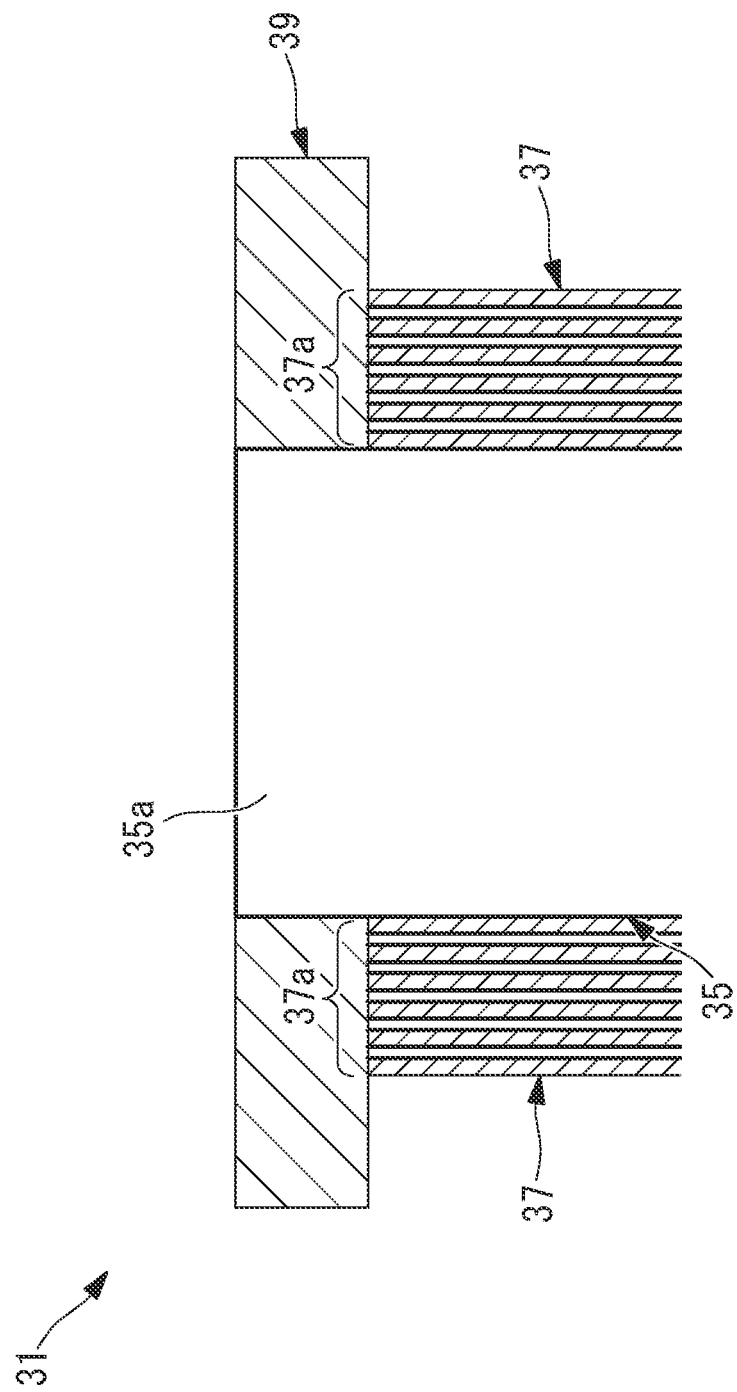
FIG. 5 is a longitudinal sectional view of a distal end portion of a conventional endoscope device.
Figure 6:
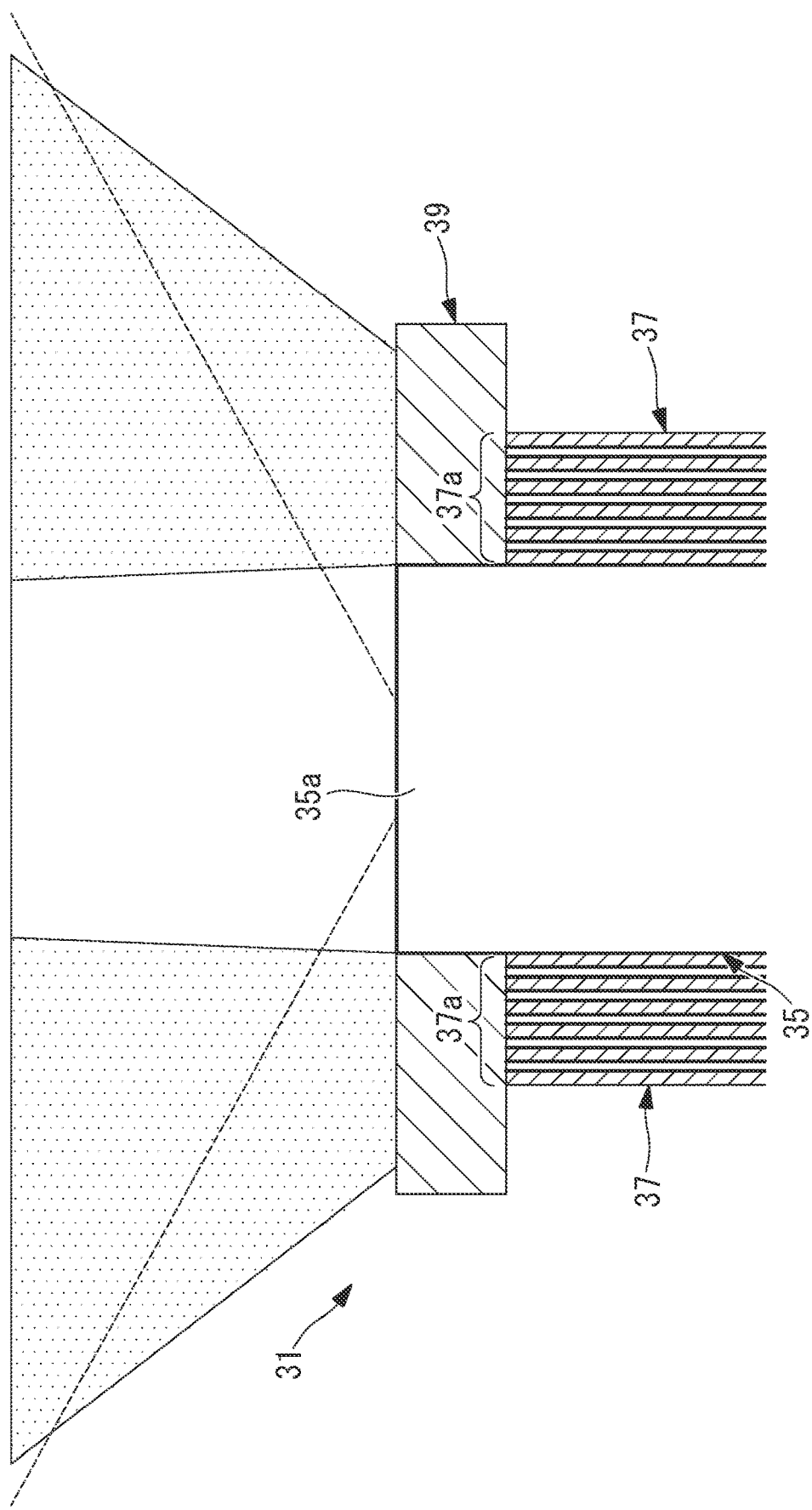
FIG. 6 is a longitudinal sectional view of the distal end portion showing a state in which illumination light is radiated toward an imaging subject from the distal end portion of the endoscope device in FIG. 5.

In this case, for example, as shown in FIGS. 5 and 6, a conventional endoscope device 31 has an objective optical system 35 that is formed in a square columnar shape having a fixed width dimension from a proximal end portion to a distal end portion 35a. Because of this, in the conventional endoscope device 31, when a distal end cover 39 is disposed at a position where distal ends 37a of light guides 37 are covered in a state in which the distal ends 37a of the light guides 37 are arranged so as to be shifted farther toward the proximal end than the distal end portion 35a of the objective optical system 35 is, illumination light emitted from the distal ends 37a of the light guides 37 is blocked by outer edges of the distal end portion 35a of the objective optical system 35 after passing through the distal end cover 39. As a result, with the conventional endoscope device 31, the illumination light is not radiated near the front side of the distal end portion 35a of the objective optical system 35, whereby vignetting of the illumination light occurs.

In contrast, with the endoscope device 1 according to this embodiment, as shown in FIG. 1, the objective optical system 5 is formed so as to be narrower toward the front side from the distal ends 7a of the light guides 7 by means of the notched portions 13 provided at the distal-end outer edges of the side surfaces of the objective optical system 5, the side surfaces being adjacent to the light guides 7, and in addition, the bulging portions 9b of the distal end cover 9 bulge toward the notched portions 13 of the objective optical system 5 from the distal ends 7a of the light guides 7. Thus, as shown in FIG. 2, the illumination light emitted from the distal ends 7a of the light guides 7 is radiated onto the imaging subject also from the bulging portion 9b sides of the distal end cover 9 without being blocked by the distal-end outer edges of the objective optical system 5. By doing so, it is possible to expand the light distribution to the front side of the distal end surface 11 of the objective optical system 5 by means of the notched portions 13 of the objective optical system 5, while physically preventing the objective optical system 5 from falling off by means of the bulging portions 9b of the distal end cover 9.

Therefore, with the endoscope device 1 according to this embodiment, it is possible to prevent the objective optical system 5 from falling off, and also to reduce illumination nonuniformity due to the influence of parallax in the proximity of an imaging subject without increasing the diameter of a distal end of an endoscope. Because the notched portions 13 are formed outside the effective incident range 11a of the objective optical system 5, it is not necessary to reduce the effective incident range 11a of the objective optical system 5, and it is possible to expand the light distribution of the illumination light without degrading the optical performance of the objective optical system 5. With the light blocking portions 15, the illumination light emitted from the distal ends 7a of the light guides 7 is prevented from entering the objective optical system 5 from the notched portions 13 after passing through the bulging portions 9b of the distal end cover 9, whereby the occurrence of flare can be prevented.

This embodiment can be modified as follows.

Figure 7:
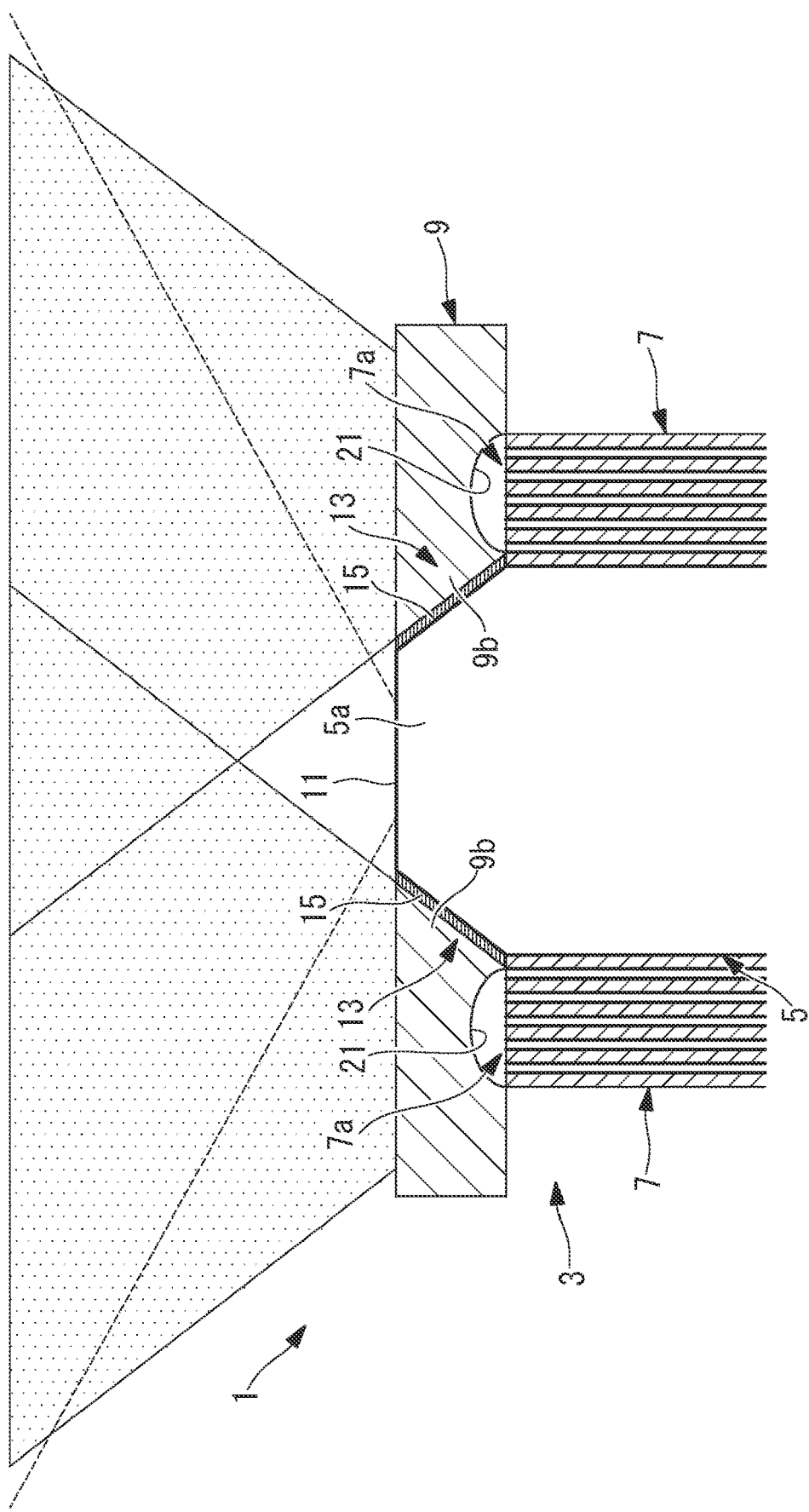
FIG. 7 is a longitudinal sectional view of a distal end portion showing a state in which illumination light is radiated toward an imaging subject from the distal end portion of an endoscope device according to a first modification of the embodiment of the present invention.

As a first modification, for example, as shown in FIG. 7, the distal end cover 9 may have recessed portions 21 that are recessed in the thickness direction in the surfaces thereof facing the distal ends 7a of the light guides 7. The recessed portions 21 may be formed in, for example, an inner spherical surface shape. Hemispherical spaces are formed between the distal ends 7a of the light guides 7 and the recessed portions 21 of the distal end cover 9.

With the endoscope device 1 according to this modification, the illumination light emitted from the distal ends 7a of the light guides 7 passes through the distal end cover 9 via the recessed portions 21, and thus, the diffusion effect of the illumination light can be improved. By doing so, it is possible to expand the light distribution of the illumination light in a more efficient manner.

Figure 8:
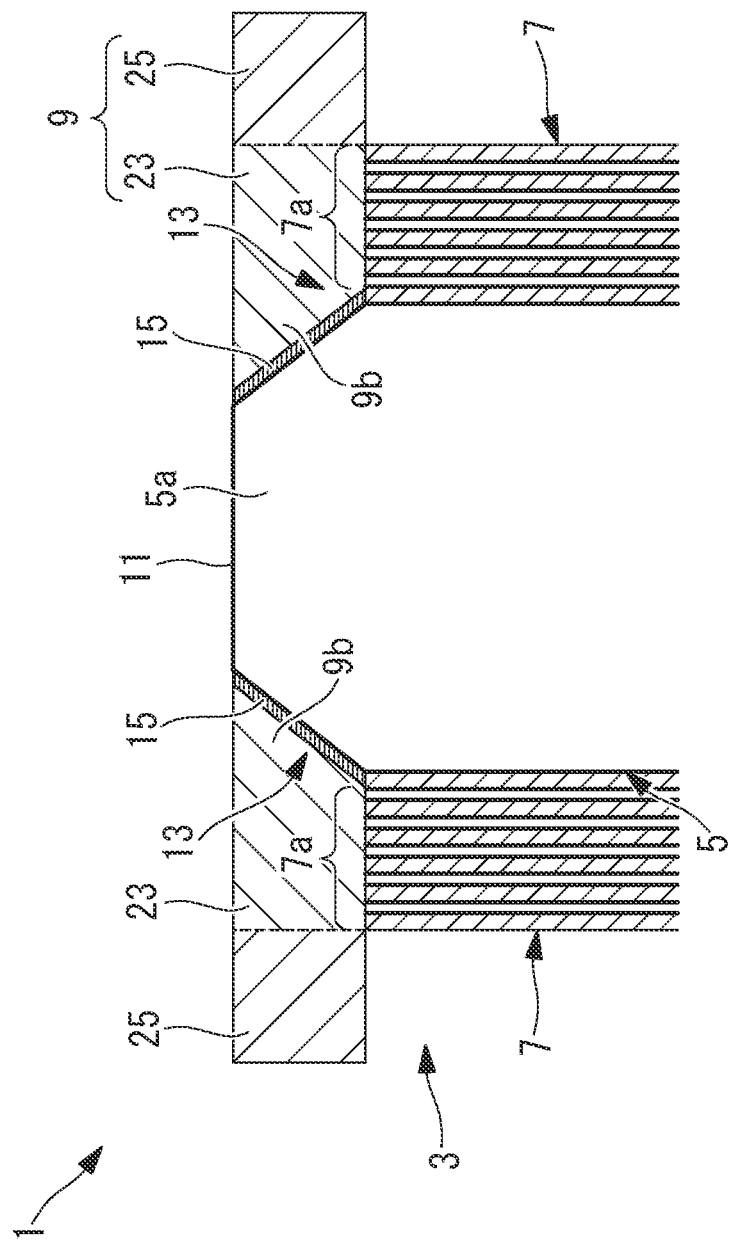
FIG. 8 is a longitudinal sectional view of a distal end portion of an endoscope device according to a second modification of the embodiment of the present invention.

As a second modification, for example, as shown in FIG. 8, at least regions of the distal end cover 9, which are arranged in front of the distal ends 7a of the light guides 7, and the bulging portions 9b may be formed of transparent resins 23, and other regions of the distal end cover 9 may be formed of opaque resins 25 having a lower transmittance than the transparent resins 23.

With this configuration, of the illumination light emitted from the distal ends 7a of the light guides 7, the illumination light emitted toward the front side of the distal ends 7a of the light guides 7 passes through the regions formed of the transparent resins 23 of the distal end cover 9, and the illumination light emitted in other directions passes through the regions formed of the opaque resins 25 of the distal end cover 9. Therefore, the regions formed of the transparent resins 23 suppress the loss of the illumination light emitted toward the front side of the distal ends 7a of the light guides 7, while the regions formed of the opaque resins 25 limit the light distribution. Thus, this configuration exhibits the effect of preventing halation during observation of a lumen-shaped imaging subject in which halation is likely to occur.

In this modification, as shown in FIG. 8, the boundaries between the regions formed of the transparent resins 23 and the regions formed of the opaque resins 25 may be formed so as to be substantially perpendicular to the radial direction from the outer edges of the distal ends 7a of the light guides 7. Alternatively, for example, the boundaries may be formed in a shape that gradually expands outward in the radial direction from the outer edges of the distal ends 7a of the light guides 7, from one-side ends of the distal end cover 9, which are on the distal end 7a sides of the light guides 7, toward other-side ends in the thickness direction.

In the case in which the boundaries between the regions formed of the transparent resins 23 and the regions formed of the opaque resins 25 are formed so as to be substantially perpendicular to the radial direction, the distal end cover 9 can be easily molded. In the case in which the boundaries between the regions formed of the transparent resins 23 and the regions formed of the opaque resins 25 are formed in a shape that gradually expands outward in the radial direction, the illumination light emitted from the distal ends 7a of the light guides 7 can be made to pass through the distal end cover 9 efficiently in the expanding direction.

In addition, in this modification, the refractive-index relationship between the regions arranged in front of the distal ends 7a of the light guides 7 and the bulging portions 9b may be set to be similar to the refractive-index relationship between cores and clads of the light guides 7. Specifically, the transmittance of the transparent resins 23 in the bulging portions 9b may be set to be higher than the transmittance of the transparent resins 23 in the regions arranged in front of the distal ends 7a of the light guides 7. With this configuration, reflection occurs at the interfaces between the regions arranged in front of the distal ends 7a of the light guides 7 and the bulging portions 9b. Thus, this configuration can contribute to alleviation of the light distribution parallax.

In this modification, for example, at least regions of the distal end cover 9 that are arranged in front of the distal ends 7a of the light guides 7 may be formed of optical glass, and other regions of the distal end cover 9 may be formed of the opaque resins 25 having a lower transmittance than the optical glass.

Since optical glass has a high surface hardness and the surface thereof is hard to damage, this configuration can further improve the durability.

Figure 9:
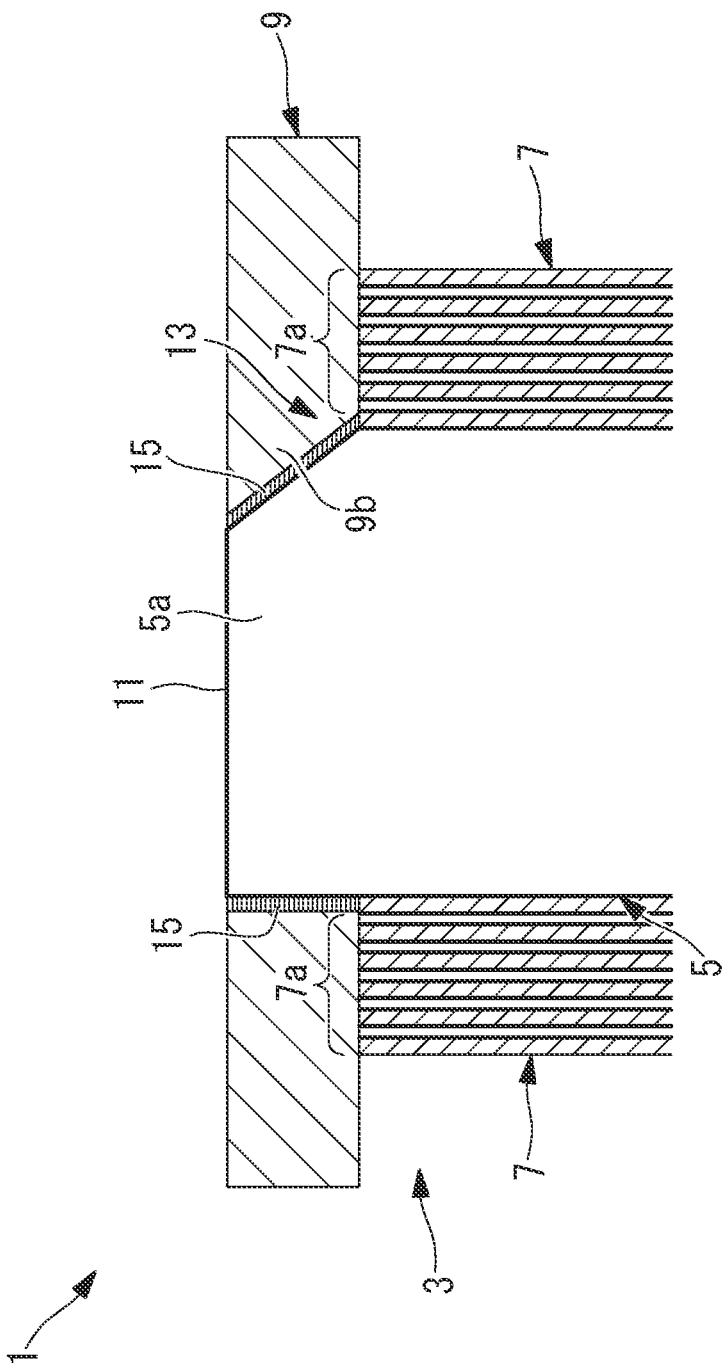
FIG. 9 is a longitudinal sectional view of a distal end portion of an endoscope device according to another modification of the embodiment of the present invention, showing a state in which a notched portion is provided only at a distal-end outer edge of a side surface of an objective optical system, the side surface being adjacent to one light guide.

In this embodiment, the distal end portion 5a of the objective optical system 5 having the notched portions 13 in front of the respective light guides 7 has been illustrated as an example; however, it suffices that the notched portion 13 be provided at the distal-end outer edge of the side surface of the objective optical system 5, the side surface being adjacent to at least one of the light guides 7. For example, as shown in FIG. 9, the notched portion 13 may be provided only at a distal-end outer edge of a side surface of the objective optical system 5, the side surface being adjacent to one of the two sets of light guides 7.

Figure 10:
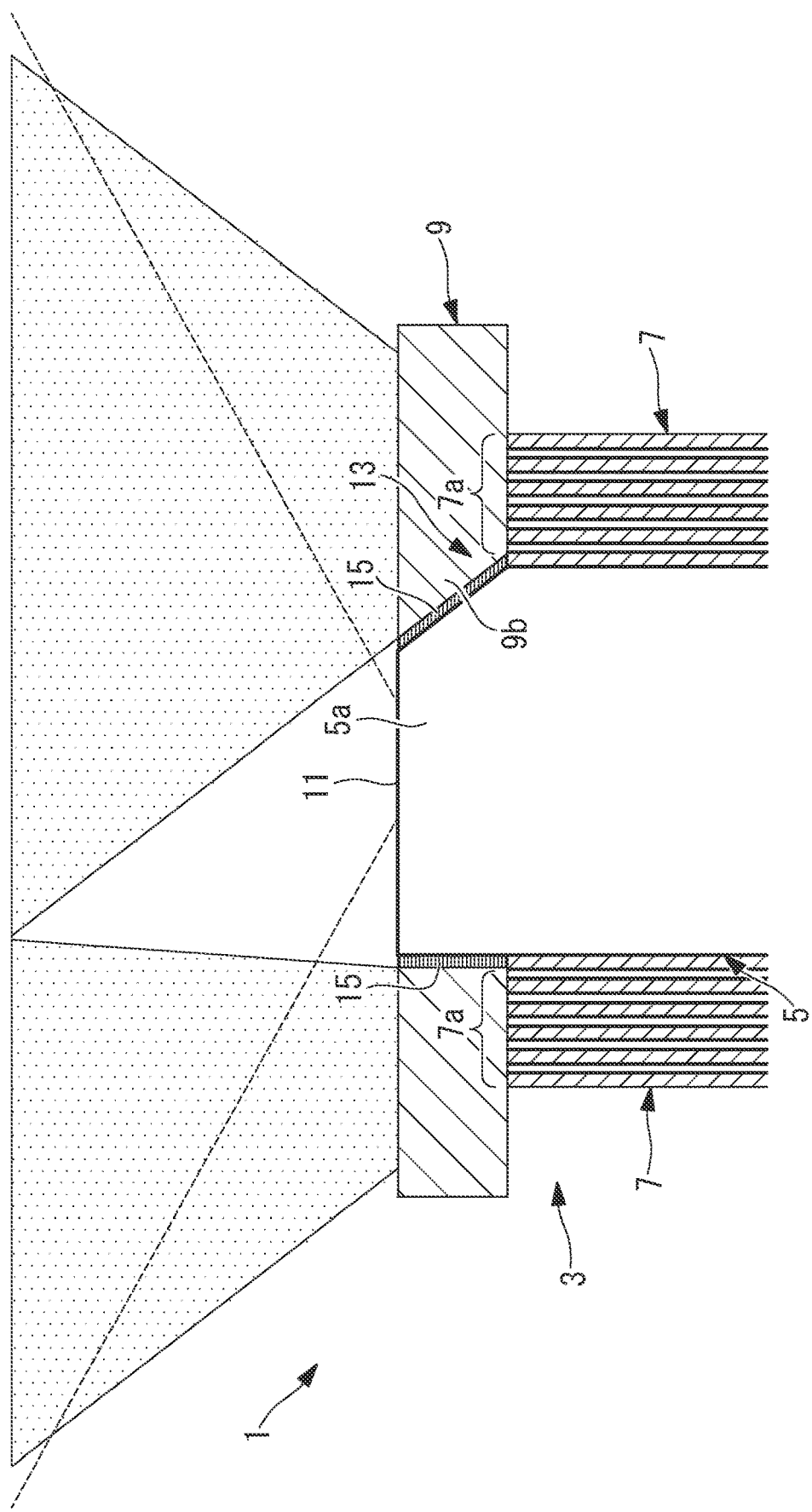
FIG. 10 is a longitudinal sectional view of the distal end portion showing a state in which illumination light is radiated toward an imaging subject from the distal end portion of the endoscope device in FIG. 9.

With this configuration also, for example, as shown in FIG. 10, the illumination light emitted from the distal end 7a of the light guide 7 in front of which the notched portion 13 is formed is radiated near the front side of the distal end surface 11 of the objective optical system 5 without being blocked by the distal-end outer edge of the objective optical system 5; thus, the occurrence of vignetting can be suppressed. In this case, it is preferable that the light blocking portion 15 be disposed also at the boundary between the distal-end outer edge of the objective optical system 5 where the notched portion 13 is not provided and the through-hole 9a of the distal end cover 9.

Although the notched portions 13 are formed by the inclined notched surfaces 13a in this embodiment, alternatively, for example, the notched portions 13 may be formed in a step shape so that the distal end portion 5a is narrower toward the front side from the distal ends 7a of the light guides 7.

Figure 11:
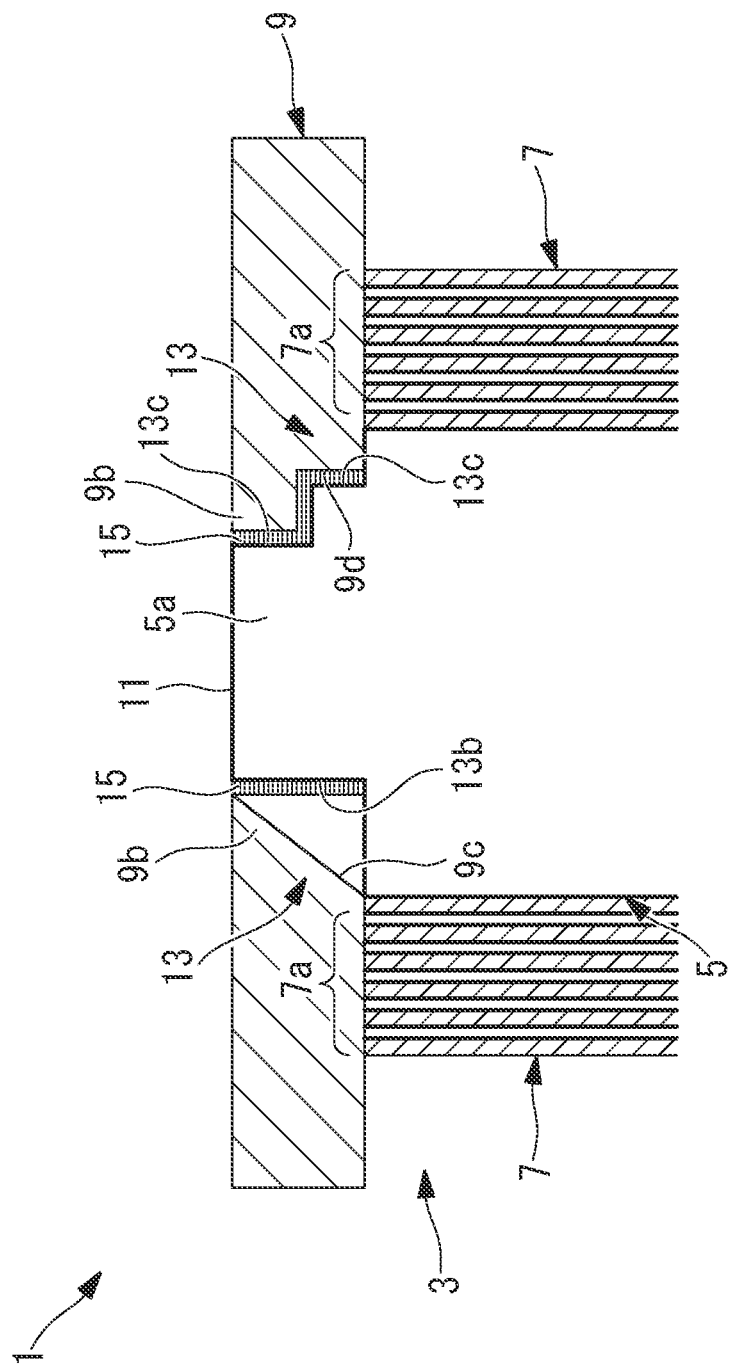
FIG. 11 is a longitudinal sectional view of a distal end portion of an endoscope device according to another modification of the embodiment of the present invention, showing an example of a notched portion formed in a step shape so that the distal end portion is narrower toward the front side from distal ends of light guides.

In this case, it suffices that the illumination light emitted from the distal ends 7a of the light guides 7 be radiated onto the imaging subject also from the bulging portion 9b sides of the distal end cover 9 without being blocked by the distal-end outer edges of the objective optical system 5. For example, as shown in FIG. 11, the notched portion 13 may be configured by a single step 13b including a surface parallel to the optical axis of the objective optical system 5 and a surface intersecting the optical axis, or the notched portion 13 may be configured by a plurality of steps 13c.

In this case also, it suffices that the bulging portions 9b hold the objective optical system 5 by being in contact with the objective optical system 5. For example, as shown in FIG. 11, the bulging portion 9b may have an inner surface 9c that is inclined in a tapered manner, or the bulging portion 9b may have a step-shaped cover inner surface 9d in conformity with the step shape of the notched portion 13.

In this embodiment, the bulging portions 9b of the distal end cover 9 have a shape in which the bulging portions 9b bulge toward the notched portions 13 over the entire area of the objective optical system 5 in the width direction; however, it suffices that the bulging portions 9b allow transmission of the illumination light emitted from the distal ends 7a of the light guides 7 while holding the notched portions 13 of the objective optical system 5. For example, the bulging portions 9b may have a shape in which the bulging portions 9b bulge toward the notched portions 13 in portions of the objective optical system 5 in the width direction.

In this embodiment, the notched portions 13 have the notched surfaces 13a having a smoothly curved shape that is recessed inward in the width direction of the distal end portion 5a of the objective optical system 5. However, alternatively, for example, the notched portions 13 may have notched surfaces 13a having a smoothly curved shape that is recessed inward in both the width direction and longitudinal direction of the objective optical system 5, or may have notched surfaces 13a having a planar shape in both the width direction and longitudinal direction of the objective optical system 5.

Although the endoscope device 1 includes the two sets of light guides 7 in this embodiment, one set or three or more sets of the light guides 7 may be employed. In this embodiment, the light guide 7 is composed of a plurality of optical fibers that are arranged side by side along the side surface of the objective optical system 5; however, alternatively, the light guide 7 may be composed of a single optical fiber.

Although the embodiment of the present invention has been described above with reference to the drawings, the specific configuration is not limited to this embodiment, and design modifications and so forth that do not depart from the scope of the present invention are also encompassed. For example, the present invention is not limited to being applied to the abovementioned embodiment and modifications and may be applied to embodiments formed by appropriately combining the abovementioned embodiment and modifications, without particular limitation.

An aspect of the present invention is an endoscope device including: an objective optical system that allows light from an imaging subject to be incident on a distal end surface and that focuses the light onto an image-capturing surface of an image-capturing element; an elongated light guide that is provided adjacent to a side of the objective optical system and that guides illumination light from a light source to be emitted from a distal end; and an optically transparent distal end cover that is disposed at a position where the distal end of the light guide is covered, wherein the distal end surface of the objective optical system is located farther forward than the distal end of the light guide, a notched portion is provided at a distal-end outer edge of a side surface of the objective optical system, the side surface being adjacent to the light guide, so that the objective optical system is narrower toward a front side from the distal end of the light guide, and the distal end cover is provided so as to bulge toward the notched portion.

With this aspect, the illumination light emitted from the light source is guided by the light guide to be emitted from the distal end thereof; the illumination light is radiated onto the imaging subject after passing through the distal end cover; the light from the imaging subject irradiated with the illumination light is made incident on the distal end surface and is focused onto the image-capturing surface of the image-capturing element by the objective optical system; and thus, it is possible to acquire image information of the imaging subject in the image-capturing element. By covering the distal end of the light guide with the distal end cover, it is possible to protect the light guide, thereby improving the durability to reprocessing.

In this case, the objective optical system is formed so as to be narrower toward the front side from the distal end of the light guide by means of the notched portion provided at the distal-end outer edge of the side surface of the objective optical system, the side surface being adjacent to the light guide, and in addition, the distal end cover bulges toward the notched portion of the objective optical system. Thus, the illumination light emitted from the distal end of the light guide is radiated onto the imaging subject also from the portion of the distal end cover bulging toward the notched portion without being blocked by the distal-end outer edge of the objective optical system. Therefore, it is possible to expand the light distribution to the front side of the distal end surface of the objective optical system by means of the notched portion of the objective optical system, while physically preventing the objective optical system from falling off by means of the distal end cover bulging toward the notched portion.

By doing so, the endoscope device according to this aspect is capable of preventing the objective optical system from falling off, and is also capable of reducing illumination nonuniformity due to the influence of parallax in the proximity of an imaging subject without increasing the diameter of a distal end of an endoscope. The notched portion of the objective optical system may be formed, at the distal-end outer edge of the objective optical system, in a tapered or step shape so that the objective optical system is narrower toward the front side from the distal end of the light guide.

The endoscope device according to the abovementioned aspect may include a light blocking portion that is disposed at a boundary between the distal end cover and the notched portion and that blocks the illumination light.

With this configuration, the light blocking portion prevents the illumination light emitted from the distal end of the light guide from entering the objective optical system from the notched portion after passing through the portion of the distal end cover bulging toward the notched portion, and thus, the occurrence of flare can be prevented.

In the endoscope device according to the abovementioned aspect, the notched portion may be formed outside an effective incident range of the distal end surface through which the light from the imaging subject, which is to be focused onto the image-capturing surface, passes.

With this configuration, it is not necessary to reduce the effective incident range of the objective optical system, and it is possible to expand the light distribution of the illumination light without degrading the optical performance of the objective optical system.

In the endoscope device according to the abovementioned aspect, the distal end cover may have a recessed portion that is recessed in a thickness direction in a surface thereof facing the distal end of the light guide.

With this configuration, the illumination light emitted from the distal end of the light guide passes through the distal end cover via the recessed portion, and thus, the diffusion effect of the illumination light can be improved.

In the endoscope device according to the abovementioned aspect, the distal end cover may be formed of a transparent resin.

With this configuration, it is possible to transmit the illumination light emitted from the distal end of the light guide toward the imaging subject while suppressing the loss of the illumination light.

In the endoscope device according to the abovementioned aspect, the distal end cover may have at least a region disposed in front of the distal end of the light guide and a region bulging toward the notched portion that are formed of a transparent resin, and may have another region that is formed of an opaque resin having a lower transmittance than the transparent resin.

With this configuration, of the illumination light emitted from the distal end of the light guide, the illumination light emitted toward the front side of the distal end of the light guide passes through the region formed of the transparent resin of the distal end cover, and the illumination light emitted in other directions passes through the region formed of the opaque resin of the distal end cover. Therefore, the transparent resin suppresses the loss of the illumination light emitted toward the front side of the distal end of the light guide, while the opaque resin limits the light distribution. Thus, this configuration exhibits the effect of preventing halation during observation of a lumen-shaped imaging subject in which halation is likely to occur.

The refractive-index relationship between the region disposed in front of the distal end of the light guide and the region bulging toward the notched portion may be set to be similar to the refractive-index relationship between a core and a clad of the light guide. Specifically, the transmittance of the transparent resin in the region bulging toward the notched portion of the objective optical system may be set to be higher than the transmittance of the transparent resin in the region disposed in front of the distal end of the light guide. With this configuration, reflection occurs at the interface between the region disposed in front of the distal end of the light guide and the region bulging toward the notched portion. Thus, this configuration can contribute to alleviation of the light distribution parallax.

In the endoscope device according to the abovementioned aspect, the distal end cover may have at least a region disposed in front of the distal end of the light guide and a region bulging toward the notched portion that are formed of optical glass, and may have another region that is formed of an opaque resin having a lower transmittance than the optical glass.

Since optical glass has a high surface hardness and the surface thereof is hard to damage, this configuration can further improve the durability.

REFERENCE SIGNS LIST 1 endoscope device
5 objective optical system
5a distal end portion
7 light guide
9 distal end cover
9b bulging portion
11 distal end surface
11a effective incident range
13 notched portion
15 light blocking portion
21 recessed portion

The invention claimed is:

1. An endoscope comprising:
   an objective optical system comprising a lens;
   a light guide provided adjacent to a first outer circumferential side of the objective optical system and configured to guide illumination light from a light source; and
   an optically transparent distal end cover disposed distally relative to the light guide and configured to cover a distal end of the light guide,
   wherein:
   a distal end surface of the objective optical system is located distally relative to the distal end of the light guide,
   the objective optical system comprises a notched portion at a distal-end outer edge of the objective optical system,
   the notched portion forms a first tapered surface at the distal-end outer edge of the objective optical system,
   the distal end cover comprises a second tapered surface on an inner circumference of the distal end cover, and
   the second tapered surface is circumferentially adjacent to the first tapered surface.

2. The endoscope according to claim 1, further comprising a light blocking surface disposed at a boundary between the distal end cover and the notched portion and configured to block the illumination light.

3. The endoscope according to claim 1, wherein the notched portion is formed outside an effective incident range.

4. The endoscope according to claim 1, wherein the distal end cover has a recessed portion recessed in a longitudinal direction in a surface thereof facing the distal end of the light guide.

5. The endoscope according to claim 1, wherein the distal end cover is formed of a transparent resin.

6. The endoscope according to claim 1, wherein:
   the distal end cover has at least a region protruding toward the notched portion, the region being formed of a transparent resin, and
   the distal end cover has another region that is formed of an opaque resin having a lower transmittance than the transparent resin.

7. The endoscope according to claim 1, wherein:
   the distal end cover has a region protruding toward the notched portion, the region being formed of optical glass, and
   the distal end cover has another region that is formed of an opaque resin having a lower transmittance than the optical glass.

8. The endoscope according to claim 1, wherein an edge of a region of the distal end cover is formed to have a convex shape, the region protruding toward a center of the objective optical system.

9. The endoscope according to claim 1, wherein the lens includes the notched portion.

10. An insertion portion for use in an endoscope, the insertion portion comprising:
    an objective optical system comprising a lens;
    a light guide provided adjacent to a first outer circumferential side of the objective optical system and configured to guide illumination light from a light source; and
    an optically transparent distal end cover disposed distally relative to the light guide and configured to cover a distal end of the light guide,
    wherein:
    a distal end surface of the objective optical system is located distally relative to the distal end of the light guide,
    the objective optical system comprises a notched portion at a distal-end outer edge of the objective optical system,
    the notched portion forms a first tapered surface at the distal-end outer edge of the objective optical system,
    the distal end cover comprises a second tapered surface on an inner circumference of the distal end cover, and
    the second tapered surface is circumferentially adjacent to the first tapered surface.

11. The endoscope according to claim 1, wherein the objective optical system is configured to focus light from an imaging subject which is incident on the distal end surface of the objective optical system onto an image-capturing surface of an image-capturing sensor.

12. The endoscope according to claim 1, wherein the distal end cover comprises a protrusion that protrudes toward a center of the objective optical system.

13. An endoscope comprising:
    an objective optical system comprising a lens;
    a light guide provided adjacent to a first outer circumferential side of the objective optical system and configured to guide illumination light from a light source; and
    an optically transparent distal end cover disposed distally relative to the light guide and configured to cover a distal end of the light guide,
    wherein:
    a distal end surface of the objective optical system is located distally relative to the distal end of the light guide,
    the objective optical system comprises a notched portion at a distal-end outer edge of the objective optical system,
    a diameter of a distal end of the objective optical system is smaller than a diameter of a proximal end of the objective optical system, and
    an edge of a region of the distal end cover is formed to have a convex shape, the edge protruding toward a center of the objective optical system.

14. The endoscope according to claim 13, further comprising a light blocking surface disposed at a boundary between the distal end cover and the notched portion and configured to block the illumination light.

15. The endoscope according to claim 13, wherein the notched portion is formed outside an effective incident range.

16. The endoscope according to claim 13, wherein the distal end cover has a recessed portion recessed in a longitudinal direction in a surface thereof facing the distal end of the light guide.

17. The endoscope according to claim 13, wherein the distal end cover is formed of a transparent resin.

18. The endoscope according to claim 13, wherein:
    the distal end cover has a region protruding toward the notched portion, the region being formed of a transparent resin, and
    the distal end cover has another region that is formed of an opaque resin having a lower transmittance than the transparent resin.

19. The endoscope according to claim 13, wherein:
    the distal end cover has a region protruding toward the notched portion, the region being formed of optical glass, and the distal end cover has another region that is formed of an opaque resin having a lower transmittance than the optical glass.

20. The endoscope according to claim 13, wherein the notched portion comprises a proximal portion located distally relative to the distal end of the light guide.

* * * * *